United States Patent [19]

Usui

[11] Patent Number: 5,084,986
[45] Date of Patent: Feb. 4, 1992

[54] DISPOSABLE WARMER HOLDER

[75] Inventor: Akio Usui, Tochigi, Japan

[73] Assignee: Mycoal Warmers Company Limited, Tochigi, Japan

[21] Appl. No.: 635,815

[22] Filed: Jan. 2, 1991

Related U.S. Application Data

[63] Continuation of Ser. No. 287,736, Dec. 21, 1988, abandoned.

[30] Foreign Application Priority Data

Dec. 22, 1987 [JP] Japan .................. 62-322689
Nov. 14, 1988 [JP] Japan .................. 63-285901

[51] Int. Cl.$^5$ .................. A61F 7/08; A43B 7/02; A43B 7/04
[52] U.S. Cl. .................. 36/2.6; 36/10; 36/43; 126/204

[56] References Cited

U.S. PATENT DOCUMENTS

| | | | |
|---|---|---|---|
| 1,970,081 | 8/1934 | Eisendrath | 126/206 X |
| 3,493,986 | 2/1970 | Erwin | 36/2.6 X |
| 3,906,185 | 9/1975 | Gross et al. | 36/2.6 X |
| 3,946,193 | 3/1976 | Giese | 36/2.6 X |
| 4,023,282 | 5/1977 | Ziegelhaefer | 36/2.6 |
| 4,094,080 | 6/1978 | Sanders | 36/2.6 |
| 4,229,319 | 2/1981 | Yoshida | 36/10 |
| 4,331,731 | 5/1982 | Seike et al. | 36/44 X |
| 4,366,804 | 1/1983 | Abe | 126/204 X |
| 4,516,564 | 5/1985 | Koiso | 126/204 X |
| 4,658,515 | 4/1987 | Oatman | 36/2.6 X |

FOREIGN PATENT DOCUMENTS

| | | | |
|---|---|---|---|
| 3544856 | 10/1986 | Fed. Rep. of Germany | 36/2.6 |
| 59-140730 | 9/1984 | Japan | . |
| 61-8013 | 1/1986 | Japan | . |
| 2092302 | 4/1990 | Japan | 36/2.6 |

Primary Examiner—Stuart S. Levy
Assistant Examiner—Joseph A. Rhoo
Attorney, Agent, or Firm—Frishauf, Holtz, Goodman & Woodward

[57] ABSTRACT

A holder for a disposable pocket warmer of chemical or oxidation exothermic type is adapted to be inserted into shoes. The holder containing the pocket warmer is made small so as to be situated only in the toe and the broadest portion of the interior of the shoe. The holder does not extend to the heel of the shoe, so that only a few different sizes of holders can be used for a wide range of shoe sizes. The holder comprises a lower base member and an upper closure or cover member bonded to each other to form a pocket to receive the warmer. Each respective member has a different permeability, so that the holder may be turned upside down or reversed, to thereby change the permeability of a member exposed to air within the shoe interior. As a result, the heating value from the pocket warmer can be changed according to environment.

8 Claims, 1 Drawing Sheet

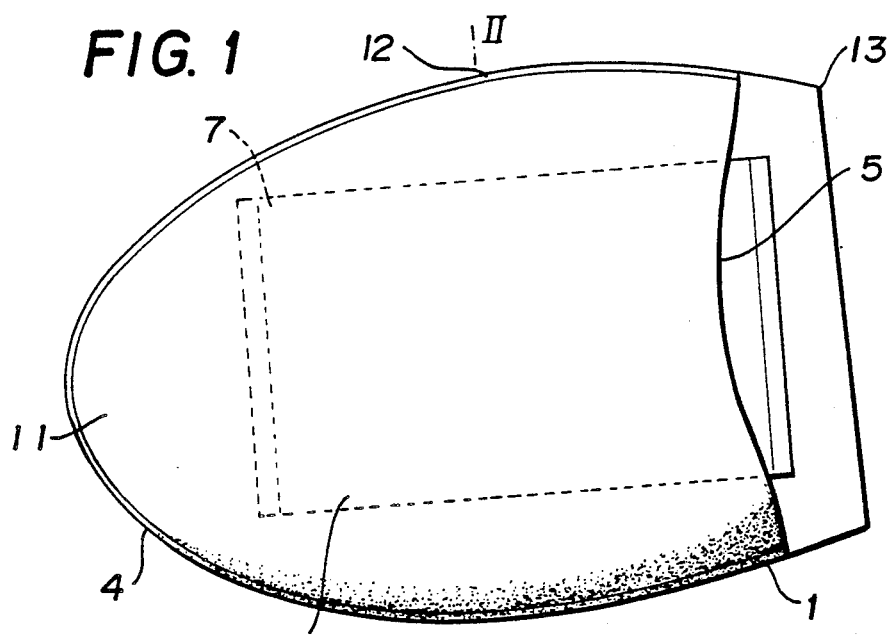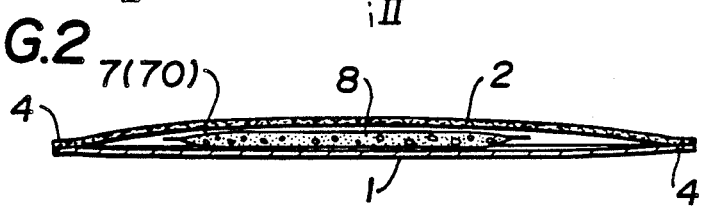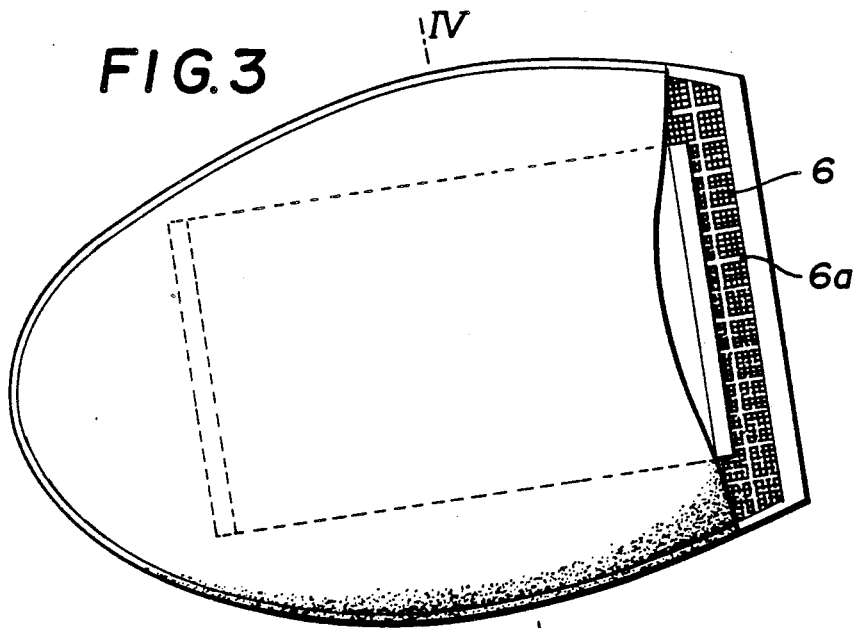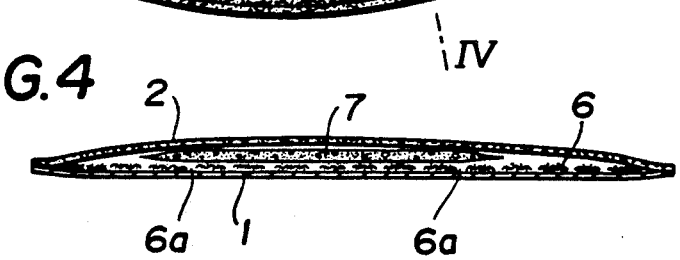

DISPOSABLE WARMER HOLDER

This application is a continuation of application Ser. No. 07/287,736, filed Dec. 21, 1988, now abandoned.

BACKGROUND OF THE INVENTION

This invention relates to a holder for a small-size disposable warmer, and more particularly, to a holder adapted to be used for applying a small disposable warmer of a chemical exothermic reaction type within the interior of footwear, such as a shoe.

Small disposable warmers employing, for example, an oxidation reaction of iron powder with the atmosphere, have been widely used, and there have been several proposals, for applying such a disposable warmer to footwear, such as a shoe or boot.

Japanese Utility Model Laid-Open Publication No.61(1986)-8013, for example, describes how to make a pocket portion for containing a disposable warmer in an inner matting placed in the interior of a shoe, and how to set an air permeable bag containing an exothermic material into the pocket portion. U.S. Pat. No. 4,249,319 discloses forming of a warmer containing portion in the upper portion of a slipper-like footwear in order to contain a small disposable warmer to give a warming effect from above toward the front portion of the foot of a wearer In a conventional footwear item, provided with an inner matting which has a disposable warmer containing portion, such as those mentioned above, the inner matting has a considerably large size so as to spread over the whole area of the footwear or shoe's bottom, resulting in a high cost. It is apparent that various sized shoes must be manufactured so as to be comfortably used by particular persons. As a result, it is necessary to stock inner mattings of various sizes in shoe stores and wholesale dealers. Manufacturing these various sized inner mattings is troublesome and necessitates large warehouse space, resulting in an increase in cost over the conventional inner mattings provided with disposable warmers.

The footwear described in U.S. Pat. No. 4,249,319 does not have such a inconvenient inner matting. However, the warming or heating effect from the warmer contained therein is given only to the upper surfaces of the wearer's feet and not given to the tips of the toes and the bottom portions of the wearer's feet. That is, in general, warm air is naturally apt to rise and resultantly the warming effect is likely to concentrate on the upper portion of the foot; that is, warm air does not propagate to the bottom portion of the footwear and accumulates in the upper interior space of the footwear. Because some interior space is kept between the inner surface or instep of the wearer's foot during walking and warmness accumulated in the space is apt to dissipate through a wall of the footwear's upper portion to the atmosphere, the wearer's feet cannot take the warmness from the warmer.

According to the prior art footwear of U.S. Pat. No. 4,249,319, the disposable warmer containing portion or holder for the small warmer is always applied and fixed to the interior of the footwear, so that in the seasons of summer and warm spring and fall, the holder is an obstruction and is felt by the wearer when the wearer's feet are placed in such footwear and disturbs the putting on of the footwear by the wearer.

It is very difficult to apply a regular-sized disposable warmer in the particular holder attached in an interior of particular shoes, such as boots, since such footwear has a portion wholly covering the overall instep and accommodating the heel. Practically, it is impossible to use a regular disposable warmer in such a shoe. It has been inevitable that large size holders are necessary for the particular shoes, resulting in the need for many manufacturing processes to make the holder and attach it to the interior of the boots. The boots will thus be expensive.

It is therefore an object of this invention to provide a compact holder for a small disposable warmer, which holder is adapted to be attached in the interior of a shoe for containing the disposable warmer in order to give a suitable and sufficient warming effect to the wearer's feet, which holder can be applied to all shoes of various sizes, and which can be produced at low cost.

SUMMARY OF THE INVENTION

According to the present invention, a compact holder for a disposable warmer containing a chemical exothermic compound, for example, of iron powder adapted to be reacted with oxygen in the atmosphere to generate heat, is applied or inserted between the sole and the instep of a shoe so as to be placed at the front half portion of the interior of the shoe.

After the compact holder of the present invention containing the disposable warmer above is set at the toe or in front of the widest portion of the sole of the shoe, the circumference of the widest portion of the compact holder firmly engages the outer wall of the holder so as to be prevented from moving or being pulled out of its front portion when walking on the shoes.

In accordance with the present invention, a holder for a disposable warmer comprises a permeable base member of a length which extends from a toe portion to a rear end portion at the mid-portion between the widest part and the heel part of the sole of a footwear, and a permeable closure member placed on the base member so as to wholly overlap and be joined to the base member through their peripheral edges leaving an inlet-and-outlet at the rear end of the holder, wherein the permeability of the base member and the closure member are different from each other and the holder can be reversibly applied to the footwear.

During use, the wearer walks on such footwear provided with such a disposable warmer containing holder, warmth from the disposable warmer is given to the tips of the toe of the wearer and eventually the whole foot is thoroughly warmed.

The permeability of the base member differs from that of the closure member of the warmer holder and the holder is turned over at a suitable time, so that all warmth of the warmer can be effectively used.

Because the warmer holder of the present invention is set and placed at only the toe of footwear, it is adaptable to all shoes of various sizes. Applying it to large size shoes, the circumferential portions of the holder engage the outermost wall of the widest portion of the shoe and is firmly attached thereto. For small size shoes, the side peripheral portions of the holder are pressed against the sides of the shoe interior space and bent, so the holder is stably located.

By selecting a material of suitable rigidity and using it as a base member of the holder, the side portions of the holder are stretched with a suitable force against the inner side wall of the shoe.

Other objects of the present invention will become apparent from the following description of the embodiments with reference to the accompanying drawings:

BRIEF DESCRIPTION OF THE DRAWINGS

FIG. 1 is a perspective view from above and front of a first embodiment of the disposable warmer holder according to the present invention;

FIG. 2 is a transverse sectional view of the disposable warmer holder arrangement of FIG. 1, taken along line II—II in FIG. 1;

FIG. 3 is a perspective view from above and front of a second embodiment of the disposable warmer holder; and FIG. 4 is a sectional view of the warmer arrangement of FIG. 2, taken along line IV—IV in FIG. 3.

DETAILED DESCRIPTION OF THE INVENTION

As shown in FIGS. 1 and 2, a holder for a disposable warmer is manufactured by joining or fastening a closure member 2 to a base member 1 along the circumferential joining portions 4 thereof. The base member 1 has a toe portion 11, a widest portion 12, and an edge 13 which ends about midway between the widest portion 12 and a heel of the sole. Thus, as seen in FIGS. 1 and 3, the holder is about one-half the length of a shoe and can be termed a "half-size" holder. The length of the base member 1 can be freely determined depending upon use. The circumferential joining portion 4 between the closure member 2 and the base member 1 is left open at the rear end or back edge to form an inlet-and-outlet 5 through which a disposable warmer 7 is inserted and pulled out. Ordinarily, the rear end portion 13 of base member 1 is cut along a straight line, however it may be cut in a curved line, such as that of an arc of a circle indented toward the front portion or toe portion 11 of the holder.

According to the present invention, the base member 1 and the closure member 2 are made of two kinds of permeable materials. For example, they are made of felt and non-woven fabric, which are different from each other in their compactness and thickness, resulting in the provision of the base member 1 and the closure member 2, respectively having permeabilities which differ from each other. The case in which the base member 1 of the holder is applied onto the bottom or sole of the shoe is different from another case in which the closure member 2 is made to contact with the sole in an air volume supplied to the disposable warmer 7 through these different materials from which these members are made. Consequently, the heating value from the disposable warmer can be changed without difficulty by reversing the orientation of the holder in the interior of the shoe. It is easy experimentally to obtain a thermal difference of about 5°-10° C. and it may be possible to change the heating value of the disposable warmer 7 in a range of from 3°-20° C.

As shown in FIG. 3, it is preferable to provide a net-like member 6 at the rear edge of the holder, which member 6 is made of, for example, a thick fabric material or yarn of a diameter: 0.1-0.5 mm. The fabric material has a considerable and suitable rigidity, and is made of a material such as vinylidene chloride and polypropylene yarn which are crossed or woven onto the base member 1 made of permeable fabric material. As shown in FIG. 4, the mesh-like member 6 has bent and curved portions 6a formed thereon in order to leave some space or clearance between the net-like member 6 and the sole of the shoe. Thus, enough air may enter in the holder through the space or clearance mentioned above, so that the disposable warmer obtains a uniform supply of air and burns or oxidizes uniformly.

Preferably, felt or non-woven fabric material from which the closure member 2 is made has a comfortable and soft touch to the sole or feet of the wearer. The net-like member 6 has sufficient rigidity, so that the closure member 2 and the base member 1 can be suitably extended and resultantly the holder containing a warmer can be suitably placed on the sole of a shoe.

A bonding material may be used at the joint portion 4 adhering the base member 1, the closure member 2, and the net-like member 6 all together. Alternatively, the base member 1, the closure member 2 and the net-like member 6, respectively may be made of plastic material and may be bonded to each other by a thermal melting process or welding through the joint portion 4.

It is well known that the disposable warmer 7 is contained in a bag 70 made of cloth or fabric having permeability, and an exothermic powder and particle compound 8. The disposable warmer 7 is adapted to be inserted into the holder through the inlet-and-outlet 5.

According to the present invention, the disposable warmer contained in the bag 70 engages with the curved portions 6a of mesh-like member 6, even though the wearer of the shoe containing a disposable warmer holder may walk rapidly. The warmer's bag 70 suitably engages also with the upper closure member 2 made of felt, resulting in a stable positioning of the bag 70 in the holder of the present invention. Naturally, the disposable warmer 7 radiates warmness and it is uniformly distributed around the feet of the wearer in order to effectively warm-up the complete foot, including the toes, when the disposable warmer 7 contained in the bag 70 is inserted into the holder positioned on the bottom of the interior of the shoe.

As mentioned above, it is necessary to reverse the disposable warmer 7 together with the holder in which the warmer is received. The holder is set at the front half of the shoe sole, so any change or variation in shape of the closure member 2 and the base member i does not hinder the suitable and stable positioning of the holder. It is recommended to apply a holder of a right foot to a left foot and vice versa after these holders are reversed, to obtain better fittability of the holders to both shoes.

It is noted that the disposable warmer holders of the present invention can be applied to various types of footwear, such as shoes and boots, of various sizes by using a pair of holders of only one size. Accordingly, it is not necessary to prepare a large number of disposable warmer holders for various sized shoes. Practically, it is possible to provide suitable fit for substantially any size of shoes by manufacturing disposable warmers, for example, of only three kinds, namely: men's size, women's size, and children's size. In consequence, it is easy to mass produce the disposable warmer holder and monitor the quality and production of them. Since the disposable warmer holder has a very small size corresponding to only the toe or front portion of a shoe, it is mass produced at a very low cost.

While specific embodiments have been described, variations thereto will occur to those skilled in the art within the scope of the present inventive concepts defined by the following claims.

I claim:

1. A half-size holder for a disposable warmer for a shoe, and which is substantially immovable in a shoe, the holder comprising:

a permeable base member which has a length of about one-half the length of a shoe in which it is to be used, said length of said base member extending from a toe portion of said base member to a rear end portion of said base member, said base member having a widest part intermediate said toe portion and said rear end portion, said rear end portion of said base member being situated at a substantially mid-position between said widest part of said base member and a heel of a shoe;

a permeable closure member mounted on said base member so as to overlap said base member, said closure member being joined to said base member along peripheral edges thereof, leaving an inlet-and-outlet opening at the rear end portion of said holder for receiving a disposable warmer through said opening and for permitting insertion and removal of said disposable warmer through said opening;

said holder being substantially flat and generally in the shape of a forward or toe portion of a shoe, and said holder being mountable to a sole portion of a shoe at a forward portion of the shoe without extending to the heel portion of the shoe, with the widest intermediate part of said base member being arranged so as to be in substantially a widest part of the forward or toe portion of a shoe;

said base member comprising a fabric material layer, and a net member made of plastic material mounted thereon and interposed between said fabric material layer and said closure member, said net member having an irregular construction defining an unevenness along its thickness direction to define spaces so that said base member and said net member hold much air, said net member defining an uneven horizontal surface;

said base member and said closure member having permeability values which are different from each other; and said holder having reversible means for providing different heating values to a wearer's foot, said reversible means comprising the holder which is flippable wherein said base member and said closure member have different permeability values.

2. The holder for a disposable warmer according to claim 1, wherein said fabric layer of said base member is made of rigid vinylidene chloride.

3. The holder for a disposable warmer according to claim 1, wherein a rear end portion of said base member and an end portion of said net member are bonded together, said inlet-and-outlet opening for the disposable warmer being maintained between said net member and said closure member.

4. The holder for a disposable warmer according to claim 1, wherein said base member and said closure member each have a different thickness to produce said different permeabilities.

5. The holder for a disposable warmer of a shoe according to claim 1, wherein said disposable warmer comprises oxidation exothermic material contained in a bag made of permeable fabric material of non-woven cloth.

6. The holder for a disposable warmer of a shoe according to claim 5, wherein said bag wholly envelops said oxidation exothermic material, said bag being made of plastic material which is perforated to obtain air permeabilty.

7. The holder for a disposable warmer of a shoe according to claim 6, wherein said bag is made of a plastic film.

8. The holder for a disposable warmer of a shoe according to claim 6, wherein said bag is made of a plastic fabric material.

* * * * *